(12) United States Patent
Kim

(10) Patent No.: US 7,431,712 B2
(45) Date of Patent: Oct. 7, 2008

(54) CAP OF TUBE FOR SUPPLYING LIQUID

(75) Inventor: Yong-Nyun Kim, Seoul (KR)

(73) Assignee: E-WHA Fresnius Kabi Inc., Gyeonggi-do (KR)

( * ) Notice: Subject to any disclaimer, the term of this patent is extended or adjusted under 35 U.S.C. 154(b) by 0 days.

(21) Appl. No.: 10/523,993

(22) PCT Filed: Aug. 6, 2003

(86) PCT No.: PCT/KR03/01580

§ 371 (c)(1),
(2), (4) Date: May 23, 2008

(87) PCT Pub. No.: WO2004/014477

PCT Pub. Date: Feb. 19, 2004

(65) Prior Publication Data

US 2005/0203460 A1    Sep. 15, 2005

(30) Foreign Application Priority Data

Aug. 9, 2002   (KR) ............... 10-2002-0047128
Nov. 26, 2002  (KR) ............... 10-2002-0073983

(51) Int. Cl.
*A61M 5/00* (2006.01)
(52) U.S. Cl. .................. 604/256; 604/405; 604/264
(58) Field of Classification Search ........... 604/256, 604/905, 263, 86, 284, 244, 415, 537, 88, 604/533, 246, 523, 278, 264, 197, 199, 405, 604/406; 128/205.12, 766
See application file for complete search history.

(56) References Cited

U.S. PATENT DOCUMENTS

| | | | | |
|---|---|---|---|---|
| 3,631,654 A | * | 1/1972 | Riely et al. | ............... 96/6 |
| 3,830,241 A | * | 8/1974 | Dye et al. | ............. 604/129 |
| 3,906,958 A | * | 9/1975 | Knox | ............. 604/129 |
| 4,445,896 A | | 5/1984 | Gianturco | |
| 4,571,244 A | * | 2/1986 | Knighton | ............. 604/118 |
| 4,596,557 A | | 6/1986 | Pexa | |
| 4,597,758 A | * | 7/1986 | Aalto et al. | ............. 604/256 |
| 4,624,664 A | | 11/1986 | Peluso et al. | |
| 5,045,096 A | * | 9/1991 | Quang et al. | ............... 96/155 |
| 5,125,415 A | * | 6/1992 | Bell | ............. 600/579 |
| 5,131,387 A | * | 7/1992 | French et al. | ........ 128/205.27 |
| 5,348,570 A | * | 9/1994 | Ruppert et al. | ............... 96/6 |

(Continued)

FOREIGN PATENT DOCUMENTS

EP    0 081 655 A1    6/1983

(Continued)

OTHER PUBLICATIONS

International Search Report.

*Primary Examiner*—Nicholas D. Lucchesi
*Assistant Examiner*—Laura A Bouchelle
(74) *Attorney, Agent, or Firm*—Sughrue Mion, PLLC

(57) ABSTRACT

A cap (10) connected to a liquid supplying tube (90) includes a passage, a liquid absorption member (40), and a gas permeable and liquid impermeable filter (50). The passage communicates with the tube and has open end. The liquid absorption member (40) is located with the passage. The filter (50) is mounted at the end of the passage to close the passage.

5 Claims, 3 Drawing Sheets

U.S. PATENT DOCUMENTS

| | | | | |
|---|---|---|---|---|
| 5,674,200 A | * | 10/1997 | Ruschke et al. | 604/126 |
| 5,779,674 A | * | 7/1998 | Ford | 604/126 |
| 6,013,061 A | * | 1/2000 | Kelley | 604/252 |
| 6,503,225 B1 | * | 1/2003 | Kirsch et al. | 604/126 |
| 6,520,935 B1 | * | 2/2003 | Jansen et al. | 604/111 |
| 2005/0124935 A1 | * | 6/2005 | McMichael | 604/129 |

FOREIGN PATENT DOCUMENTS

| | | |
|---|---|---|
| EP | 0 406 584 A1 | 1/1991 |
| KR | 20-0226977 Y1 | 3/2001 |
| KR | 226997 Y1 | 6/2001 |
| WO | WO 02 11971 A1 | 2/2002 |

* cited by examiner

CAP OF TUBE FOR SUPPLYING LIQUID

TECHNICAL FIELD

The present invention relates to a cap for a liquid supplying tube, and more particularly, to a cap enabling the exhaust of air existing in a tube before supplying a liquid in a state where the cap is installed in the tube.

BACKGROUND ART

Generally, a tube is connected to a liquid supplying apparatus that functions to supply a liquid medicine (or blood) into a human body. A distal end of the tube is plugged by a cap before injection of the medicine. The tube is then used by removing the cap therefrom and connecting the distal end of the tube to an inlet of a member (e.g., catheter), which has been directly connected to the human body, when the medicine is injected. Before connecting the tube to the catheter, an injection (liquid medicine) is caused to flow downward to exhaust air remaining in the tube. If air is injected into the body of a patient, a dangerous situation may occur in the patient. Generally, during the air-exhausting process, there is some loss in the liquid medicine. In such a conventional cap, it is impossible to perform sterilization with gas in a state where the cap has been installed.

A structure proposed by the present inventor in order to solve the problem is disclosed in Korean Utility Model Registration No. 20-0226977. In the proposed structure, a distal end cap is provided with an air pass filter and an air vent to conveniently exhaust air existing in a tube. That is, as a liquid medicine is supplied to the tube from a liquid supplying apparatus, air existing in the tube is pushed by the supplied liquid medicine and then moves toward the cap. Consequently, the air escapes from the tube through the air pass filter and the air vent. Since only the air escapes therefrom, it is possible to easily exhaust the air without a resulting loss in the liquid medicine. Such a structure has remarkable effects superior to those obtained by conventional caps. However, there are sometimes cases where air remains between portions of liquid medicine within the tube. In such a case where air remains between portions of liquid within the tube, the air pass filter and the air vent may become clogged with a first portion of liquid upon exhaust of the air and thus the air remaining between the portions of liquid may not be exhausted. In this case, there may be inconvenience upon exhaust of the air remaining between the portions of liquid medicine in that the cap is opened and the portion of liquid medicine prior to the air is removed, and subsequently, the cap is closed again and the air is then exhausted. To solve this inconvenience, there is a need for a further improved distal end cap enabling the exhaust of air existing between portions of liquid in a tube without separating the cap from the tube.

SUMMARY OF THE INVENTION

An object of the present invention is to provide a distal end cap having excellent effects, which further improves the structure of the existing distal end cap proposed by the present inventor, and more specifically, to provide a cap for a distal end of a tube, which can easily exhaust air that may exist between portions of liquid in the tube.

Air generally exists in a tube. When a liquid medicine is supplied to the tube, the air escapes from the tube through a distal end of the tube and the liquid medicine then reaches the distal end of the tube. Air sometimes exists just behind the portion of the liquid medicine that has first reached the distal end of the tube. The present invention provides a distal end cap that can effectively exhaust the air even in such a case. The present inventor considered that in such a case where air exists behind a portion of liquid that has first reached the distal end of the tube, the amount of the portion of liquid is small, and based on this consideration, designed a distal end cap equipped with a liquid absorption material (absorbent) that can absorb the portion of liquid.

According to an aspect of the present invention, there is provided a cap for a tube, which is connected to a distal end of the tube, and comprises a passage for communicating with the tube and the outside, a liquid absorption member disposed in the passage, and a gas permeable and liquid impermeable filter for blocking the passage at a (downstream) position farther than the liquid absorption member from the tube.

The liquid absorption member may be configured to surround the passage. The liquid absorption member may be made of a sponge material or fiber material.

The filter may be made of a porous plastic resin material.

The cap may further comprise a main body which includes an outer wall and a connection projection provided radially inward of the outer wall, and in which the other end opposite to an end of the main body with the connection projection provided thereon is open, and the passage is formed and the liquid absorption member is received; and a closure which is connected to close the other open end of the main body and includes an exhaust hole that communicates with the passage and is blocked by the filter.

The connection projection may comprise a tube extending inward and outward of the end of the outer wall, and the absorption member is fixedly fitted between the outer wall of the main body and an inward extension of the connection projection.

The closure may further comprise an extension for isolating the absorption member and the filter from each other.

The distal end cap may be connected to an injection quantity adjustor with a detachable clip installed thereon, and also connected to the clip so that they can be removed together.

According to another aspect of the present invention, there is provided a liquid medicine supplying apparatus for supplying a liquid medicine, comprising a liquid medicine reservoir; a pressure device for applying pressure to the liquid medicine stored in the liquid medicine reservoir; a tube connected to the liquid medicine reservoir; and a cap, as described above, connected to the distal end of the tube.

BRIEF DESCRIPTION OF THE DRAWINGS

For better understanding of the objects and features of the present invention by those skilled in the art, a preferred embodiment of the present invention will be described with reference to the accompanying drawings in which.

DETAILED DESCRIPTION OF THE EMBODIMENTS

Hereinafter, embodiments of the present invention will be described in detail with reference to the accompanying drawings.

Figure 1:
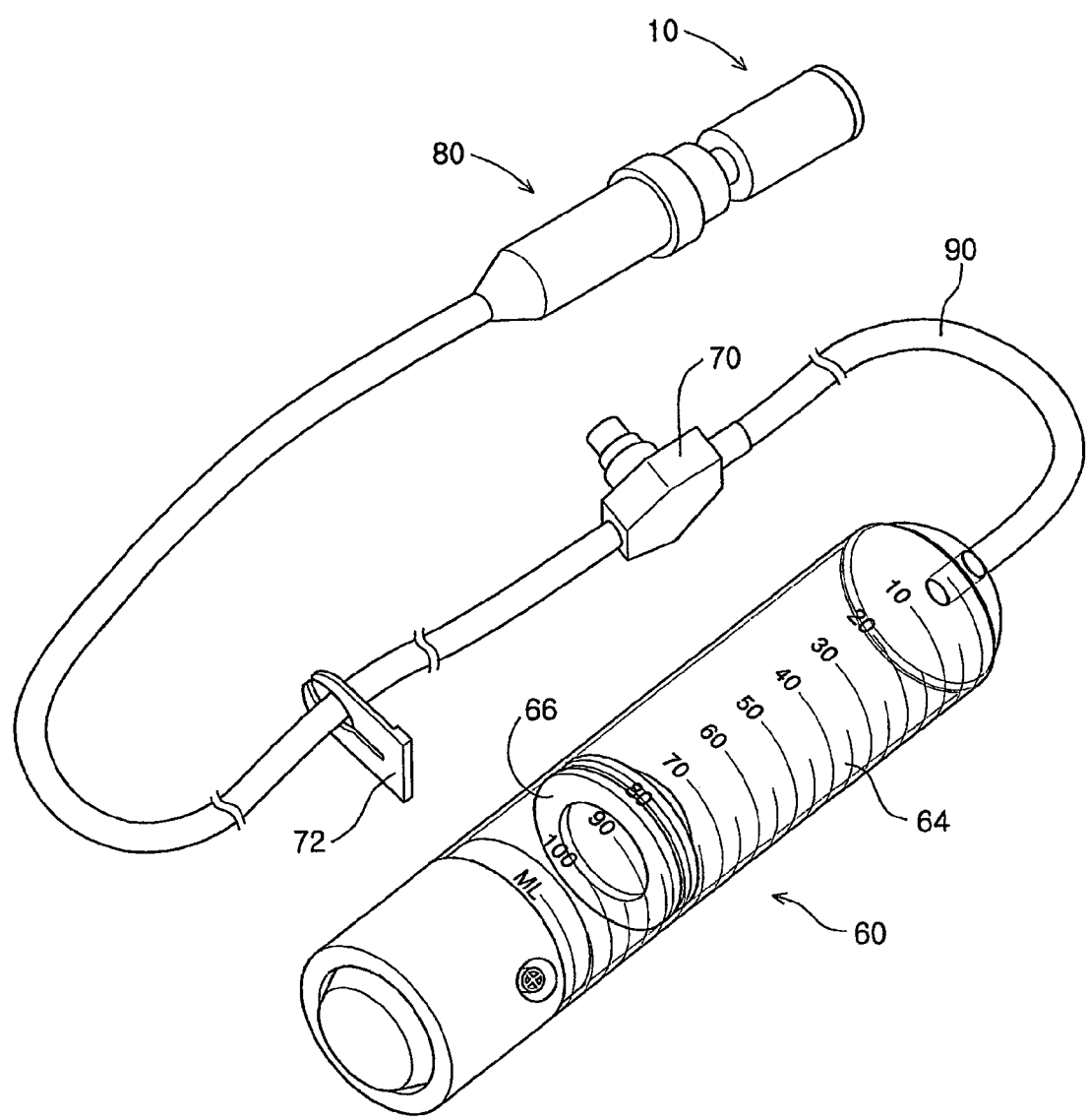
FIG. 1 is a perspective view of a liquid medicine injection apparatus equipped with a tube cap according to an embodiment of the present invention.

Referring to FIG. 1, a tube 90 is coupled to a liquid medicine injection apparatus 60. The liquid medicine injection apparatus 60 generally comprises a supply cylinder 64 and a piston 66. The piston is moved and pushes out the medicine within the cylinder while being subjected to a force by means of the elasticity of a rubber bladder, gas pressure, a push rod driven by a motor, or the like.

The tube 90 is connected to an end of the cylinder 64 of the injection apparatus 60. A passage for liquid medicine defined by the tube 90 is equipped with, for example, a supply valve 70 for supplying the medicine into the cylinder 64 before using the apparatus. A clamp 72 is also provided to cut off a stream of medicine flowing along the tube 90 if necessary. The structure of the tube connected to the injection apparatus may be that disclosed in PCT Publication No. WO 02/11791 A1, and a relevant portion of details disclosed in PCT Publication No. WO 02/11791 A1 is incorporated herein by reference. A distal end connection member 80 and a cap 10 for plugging an opening of the connection member 80 are connected to a distal end of the tube 90. When the medicine is injected into a human body, the cap 10 is removed and the connection member 80 is connected to an inlet of a member (e.g., catheter) directly inserted into the human body.

Figure 2:
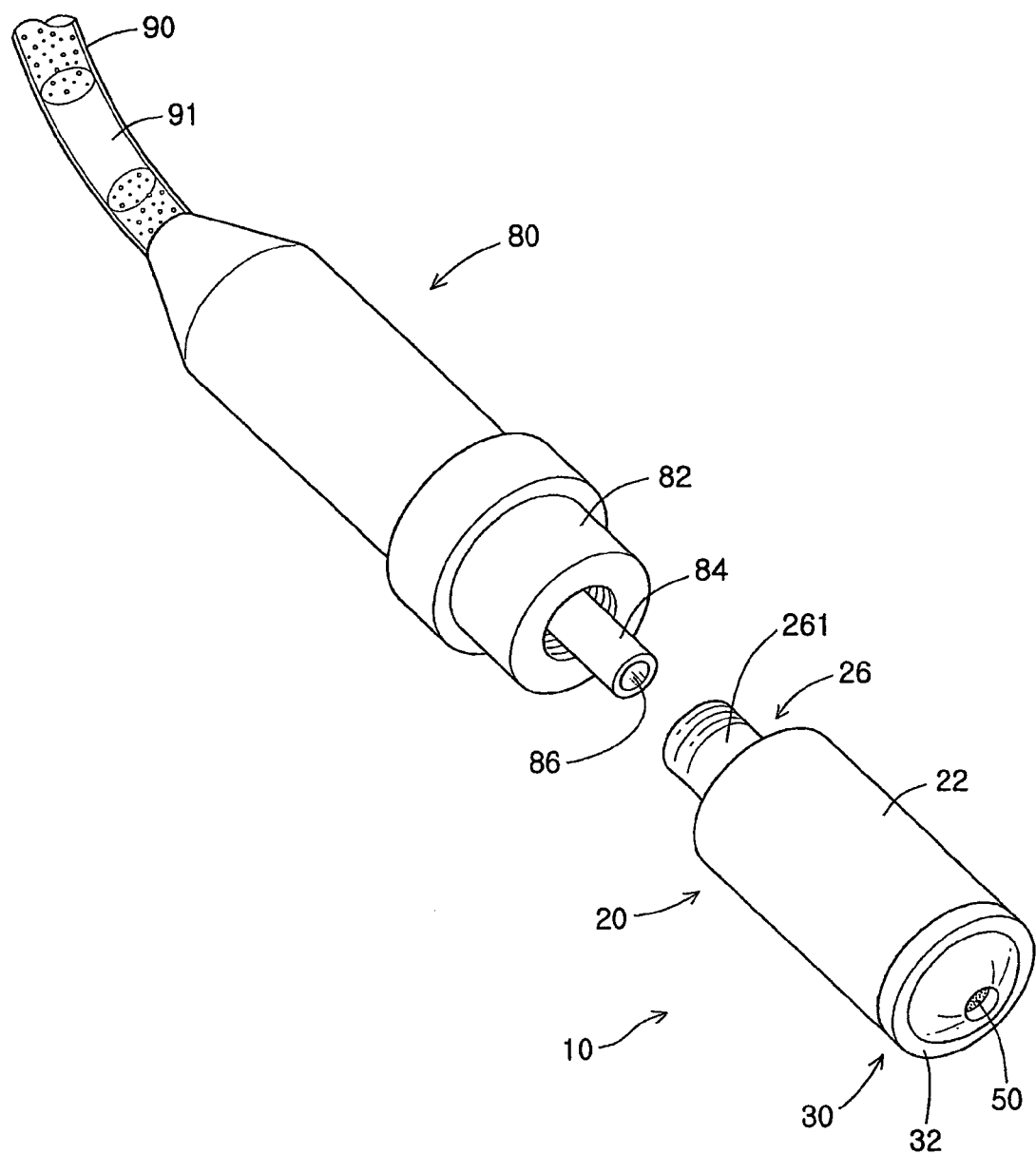
FIG. 2 is a perspective view of the tube cap shown in FIG. 1, showing a state where a tube is coupled with the cap.

Referring to FIG. 2, a cylindrical projection 84 is provided at an end of the connection member 80. The projection 84 is provided with a communication hole 86. The medicine is supplied through the hole 86. The connection member 80 is provided with a cylindrical wall 82 surrounding the projection 84. Female threads are formed on an inner surface of the cylindrical wall 82 and are to be engaged with male threads on an outward extension 261 of the cap 10 to be described later. After the cap 10 is removed, the female threads are threadably engaged with a connector of a catheter or the like. The threadably engaged portions are configured to be hermetically sealed.

Figure 3:
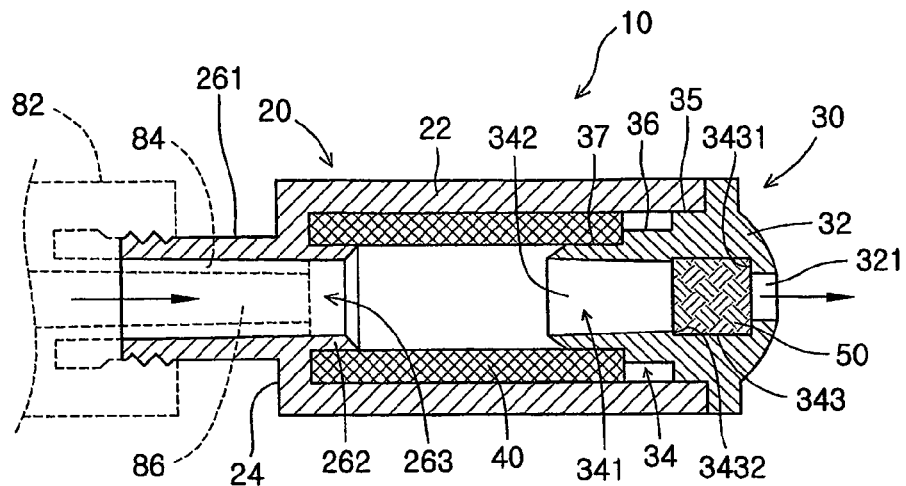
FIG. 3 is a sectional view of the tube cap shown in FIG. 1.

Referring to FIG. 2, the cap 10 substantially takes the shape of a cylinder and has one end connected to the connection member 80 at the distal end of the tube 90. Referring to FIGS. 2 and 3, the cap 10 comprises a main body 20 and a closure 30. The main body 20 takes the shape of a stepped hollow cylinder and has a cylindrical outer sidewall 22 extending to an end wall 24. An end of the main body opposite to the end wall is open and is closed with the closure 30 to be described later.

A connection tube 26 formed to axially extend in opposite directions with respect to the end wall 24 is provided at the center on the side of the end wall 24. The male threads are formed at a tip portion of the outward extension 261 of the connection tube 26 and are to be engaged with the female threads formed on the inner surface of the cylindrical wall 82 of the connection member 80. The connection tube 26 is hollowed to form a passage 263 with a circular cross section. The corresponding projection 84 of the connection member 80 is inserted into the passage 263 so that the hole 86 of the projection 84 can be in communication with the passage 263 of the connection tube 26. The passage 263 of the connection tube 26 is slightly tapered such that the diameter thereof decreases inward. This is to cause the corresponding projection 84 of the connection member 80 to be in close contact with the passage as the projection is further inserted into the passage. An inward extension 262 of the connection tube 26 that is formed to extend inward is spaced apart by a predetermined distance from the sidewall 22. A liquid absorption member 40 to be described later is tightly fitted into a space between the inward extension 262 and the sidewall 22.

Referring to FIG. 3, the absorption member 40 is a cylindrical member provided with a passage penetrating therethrough at the center thereof, i.e. an annular cylindrical member. In the present embodiment, the absorption member 40 is preferably made of a material that can absorb and hold a liquid well. Sponge that is a foam material, and fiber materials such as cloth may be used. As an example, a sponge made of melamine formaldehyde polycondensate may be used. However, the material of the absorption member in the present invention is not limited thereto. Any material that can absorb liquid well may be used. The absorption member 40 has inner and outer diameters such that it can be tightly fitted between an inner surface of the sidewall 22 and an outer surface of the inward extension 262 of the connection tube 26. An outer surface of the absorption member 40 is in contact with the sidewall 22 of the main body 20. One end of the absorption member is fixedly fitted into an annular space between the inward extension 262 of the connection tube 26 and the sidewall 22 of the main body 20. The other end of the absorption member is supported by the closure 30 to be described later.

Referring to FIGS. 2 and 3, the closure 30 comprises a circular lid 32 for covering the opening of the main body 20, and an insertion boss 34 that extends from the lid 32 and is fitted into and contained in the main body 20. The lid 32 and the insertion boss 34 are provided with an axial passage 341. An end of the axial passage 341 on the side of the lid is provided with a catching step 3431. The passage 341 is formed with a tapered portion 342 which is tapered such that the diameter thereof gradually decreases from an end of the insertion boss 34 approximately to the middle of the passage toward the lid 32, and a filter-receiving portion 343 having a substantially constant diameter slightly larger than that of the tapered portion 342 and extending from the tapered portion 342 to an air exhaust hole 321. There exists a low step 3432 formed due to differences between the diameters of the relevant ends of the filter-receiving portion 343 and the tapered portion 342. An air pass filter 50 to be described later is tightly fitted into and received in the filter-receiving portion 343. The air pass filter 50 received in the filter-receiving portion 343 does not protrude toward the tapered portion 342 by being caught by the step 3432 formed between the filter-receiving portion 343 and the tapered portion 342. The air pass filter is prevented from escaping outward by means of the catching step 3431.

Referring to FIG. 3, the insertion boss 34 comprises first to third extensions 35, 36 and 37 that are circular in cross section and have outer diameters sequentially decreased toward the end of the insertion boss. The outer diameter of the first extension 35 is determined to be in close contact with the inner surface of the sidewall 22 of the main body 20. This is to cause the insertion boss to be tightly fitted and prevent it from escaping when the closure 30 is fitted through the opening of the main body 20. Alternatively, the closure 30 may be coupled to the main body 20 by means of an adhesive so that they cannot be separated from each other. The second extension 36 has a diameter smaller than that of the first extension 35. There is a step between the first and second extensions 35 and 36.

The outer diameter of the third extension 37, which is smaller than that of the second extension 36, is determined such that the third extension can be tightly fitted into the liquid absorption member 40. There is a step between the second and third extensions 36 and 37. The third extension 37 is inserted lengthwise into the liquid absorption member 40.

An outer surface of the third extension 37 is in close contact with an inner surface of the absorption member 40, and the end of the absorption member 40 abuts on the step between the second and third extensions 36 and 37. A distal end of the third extension 37 is tapered so that it can be smoothly inserted into the absorption member 40. The third extension 37 functions to prevent the liquid absorption member 40 from abutting on the air pass filter 50 or to prevent liquid absorbed by the liquid absorption member 40 from abutting on the air pass filter 50 due to outflow of the absorbed liquid. If the liquid abuts on the air pass filter 50 or air exhaust hole 321, air cannot be properly exhausted or it takes a great deal of time to exhaust the air.

The air pass filter 50 is made of a liquid impermeable and gas permeable material and completely closes up the passage 321. That is, the air pass filter is made of a material through which liquid cannot permeate but gas can permeate. Preferably, the air pass filter 50 can be made and used by processing a porous plastic resin material having such a property into a shape suitable for the passage. Such a material for the air pass filter is available from Porex Corporation (website: www.porex.com) located at Fairbum, Ga. 30213, U.S.A. The product under the trademark "Porex Hydrophobic Vents" available from Porex Corporation may be used. This product is made of polyethyl polytetrafluoroethylene. The material for the air pass filter is also available from Micropore Plastics, Inc. located at Stone Mountain, Georgia, U.S.A. The air pass filter 50 has such elasticity that it can be slightly shrunken while being fitted into the passage 321 of the closure 30 and then can be restored to its original state in place.

Now, the operation of the cap will be described in detail with reference to FIGS. 2 and 3.

Referring to FIGS. 2 and 3, air 91 exists just behind a portion of liquid medicine, which has first reached the end of the tube, within the tube 90. The portion of liquid medicine is introduced into the cap 10 through the communication hole 86 of the connection member 80. The first introduced portion of liquid medicine is completely absorbed by the liquid absorption member 40 having liquid absorbency before it abuts on the air pass filter 50. The portion of liquid medicine that has already been absorbed by the absorption member 40 is prevented from again flowing into the air pass filter 50 by means of the third extension 37 of the closure 30. When the first introduced portion of liquid medicine is completely absorbed by the liquid absorption member 40, the subsequently introduced air 91 reaches the air pass filter 50 and then naturally and completely escapes to the outside through the liquid impermeable and gas permeable air pass filter 50 and the air exhaust hole 321. Consequently, only liquid medicine remains within the cap 10. Then, the cap 10 is rotated to be separated from the distal end connection member 80 and connected to a catheter or the like, so that only the liquid medicine with air completely removed therefrom can be supplied.

Figure 4:
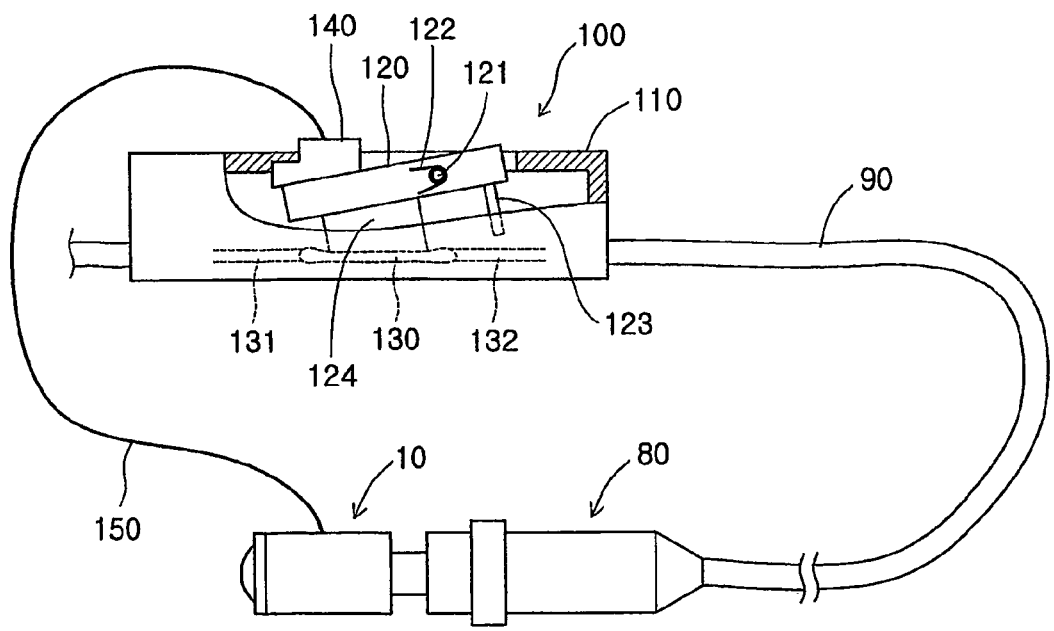
FIG. 4 is a side view of the tube cap shown in FIG. 2 and an injection quantity adjustor to which the tube cap is connected, wherein the injection quantity adjustor is partially cut away to show the interior thereof.

FIG. 4 shows a cap with a string 150 added thereto. In this embodiment, the string 150 connects the cap 10 to an elemental member of an injection quantity adjustor. In FIG. 4, a case 110 of the injection quantity adjustor 100 is partially cut away to show the interior of the injection quantity adjustor 100. Referring to FIG. 4, the distal end cap 10 is installed at the distal end of the tube 90 connected to the injection quantity adjustor 100. The liquid medicine is supplied through the injection quantity adjustor 100 and the tube 90.

The injection quantity adjustor 100 performs the function of constantly maintaining the amount of supplied liquid medicine and also performs the function of temporarily increasing the amount of supplied liquid medicine. To this end, the injection quantity adjustor 100 comprises a temporary storage bladder 130 for storing the liquid medicine, a button member 120 for pressing the storage bladder 130, and a clip 140 fitted to maintain a state where the button member 120 presses the storage bladder 130. The storage bladder 130 is connected to tubes 131 and 132 through which the liquid medicine flows in and out of the storage bladder. The tube 132 through which the liquid medicine flows out can be blocked by means of a shutter 123 of the button member 120 to be described later. The temporary storage bladder 130 is to temporarily increase the amount of supplied liquid medicine. Thus, the liquid medicine is normally supplied through another passage (not shown). The button member 120 includes a rotational shaft 121 around which a torsion spring 122 is fitted. Therefore, the button member 120 can be rotated about the rotational shaft 121 and is subjected to the force of the torsion spring 122 exerted in a direction for maintaining the state where the shutter 123 blocks the tube 132. At opposite sides of the button member 120 with respect to the rotational shaft 121, there are provided a pressing portion 124 and the shutter 123, respectively. Thus, if a portion of the button member 120 on the side of the pressing portion 124 is pressed down, the pressing portion 124 presses down and squeezes the storage bladder 130, and the shutter 123 that has blocked the tube 132 is raised to open the tube 132, as shown in the figure. Then, the liquid medicine stored in the storage bladder 130 is additionally supplied to temporarily increase the amount of supplied liquid medicine.

Meanwhile, a preparatory operation for sending the liquid medicine to the distal end of the tube 90 before the use thereof is made in a state where the storage bladder 130 has been pressed down. Thus, the clip 140 is fitted above the portion of the button member 120 on the side of the pressing portion 124 in order to maintain the state where the pressing portion 124 presses down the storage bladder 130 as shown in the figure. In other words, when the clip 140 is fitted, the storage bladder 130 is pressed by the pressing portion 124, and the tube 132, which is connected to the storage bladder 130 and through which the liquid medicine flows out, is in an opened state. In this state, when the liquid medicine is supplied from the supply cylinder 64 (see FIG. 1), the liquid medicine flows into the connection member 80 through the injection quantity adjustor 100 and the tube 90. At this time, air is removed by means of the cap 10 as described above with reference to FIGS. 1 to 3. After the air has been completely removed, the cap 10 is removed and the connection member 80 is connected to a catheter to supply the liquid medicine. At this time, the clip 140 of the injection quantity adjustor 100 should also be removed. However, if the removal of the clip is forgotten, a normal supply state of the liquid medicine cannot be maintained since the tube 132 connected to the storage bladder 130 has been opened. Therefore, it is preferred that the clip 140 be connected to the cap 10 by means of the string 150. Since the connected clip 140 can be removed together with the cap 10 upon removal of the cap 10, it is possible to securely remove the clip.

In such a case where there is a member that should be inevitably removed before supplying the liquid medicine into a human body, if the member to be removed is connected to the cap in the aforementioned manner, the member can be surely removed without forgetting about the removal of the member.

Although the present invention has been illustrated and described with reference to the exemplified embodiments of the present invention, it can be understood that various changes, modifications and additions can be made thereto without departing from the spirit and scope of the present invention.

The invention claimed is:

1. A cap for a tube in which a liquid medicine flows, said cap adapted to be detachably connected to a distal end of the tube, comprising:
    a cylindrical main body which has an outer wall, an inner wall, a first open end which is to be detachably connected to the tube, a second open end which is opposite to the first open end, and a passage for communicating with the tube and the outside, the passage being formed between the first open end and the second open end,
    an inlet port through which the medicine and air flow into the passage from the tube, the inlet port being disposed at the first open end;
    a cylindrical and hollow liquid absorption member disposed at or near the inlet port in the passage to surround the passage; and
    a gas permeable and liquid impermeable filter for blocking the passage at a position farther than the liquid absorption member from the inlet port; and
    a closure which is connected to the second open end to close the main body at the second open end and which has an exhaust hole to remove air from the passage,
    wherein the tube carries a liquid medicine from which air to be removed,
    wherein said cap is detached from the tube when supplying the medicine to a subject;
    wherein the main body further comprises a connection projection which extends from the first end of the main body and which is coupled to the tube, the connection projection having an outer wall and an inner wall, wherein the outer wall of the connection projection has a smaller diameter than the outer wall of the main body, and the connection projection has an inwardly extended protrusion toward the passage in a way to form an annular trench between the inner wall of the main body and the inwardly extended protrusion;
    wherein one end of the absorption member is fixedly fitted into an annular trench;
    wherein the closure further comprises a stepped extension toward the passage of the main body such that the stepped extension and the inner wall of the main body form a space between them, and the other end of the absorption member is fitted into the space and abuts on a step of the stepped extension; and
    the stepped extension separates the gas permeable and liquid impermeable filler from the absorption member.

2. The cap as claimed in claim 1, wherein the liquid absorption member is made of a sponge material.

3. The cap as claimed in claim 1, wherein the liquid absorption member is made of a fiber material.

4. The cap as claimed in claim 1, wherein the filter is made of a porous plastic resin material.

5. A liquid medicine supplying apparatus for supplying a liquid medicine, comprising:
    a liquid medicine reservoir;
    a pressure device for applying pressure to the liquid medicine stored in the liquid medicine reservoir;
    a tube of which one end is connected to the liquid medicine reservoir; and
    a cap according to claim 1 connected to the other end of the tube,
    the apparatus further comprising a flow control device including a member that is connected to the cap and is to be removed according to the detachment of the cap from the tube when upon supplying the liquid medicine to a subject.

* * * * *